United States Patent [19]

Libby

[11] 4,250,382
[45] Feb. 10, 1981

[54] COAT DETECTION METHOD

[75] Inventor: Craig R. Libby, Gorham, Me.

[73] Assignee: Scott Paper Company, Philadelphia, Pa.

[21] Appl. No.: 66,397

[22] Filed: Aug. 14, 1979

Related U.S. Application Data

[63] Continuation of Ser. No. 888,013, Mar. 20, 1978, which is a continuation-in-part of Ser. No. 794,760, May 9, 1977.

[51] Int. Cl.³ .............................................. G09K 3/00
[52] U.S. Cl. .................................... 250/302; 427/411
[58] Field of Search ................ 250/302; 427/411, 413

[56] References Cited

U.S. PATENT DOCUMENTS 3,956,630  5/1976  Mellows .............................. 250/302

*Primary Examiner*—Harold A. Dixon
*Attorney, Agent, or Firm*—R. Duke Vickrey; John W. Kane, Jr.

[57] ABSTRACT

Disclosed is a method of detecting a cured silicone coating applied to a paper substrate or the like in web form, comprising adding an effective amount of a fluorescent pigment to the silicone coating formulation to be applied to the substrate, applying the coating to the substrate, curing the silicone coating, scanning the coated surface of the substrate with a UV light source, and detecting the fluorescence of the coating. Also disclosed is the coated paper product with which the method of the invention can be employed.

2 Claims, 2 Drawing Figures

COAT DETECTION METHOD

This is a continuation of application Ser. No. 888,013 filed Mar. 20, 1978 for COAT DETECTION METHOD, which itself is a Continuation-In-Part of application Ser. No. 794,760, for FLUORIMETRIC COAT WEIGHT MEASUREMENT, filed May 9, 1977.

BACKGROUND OF THE INVENTION

1. Field of the Invention

The present invention relates to a method of detecting a silicone coating applied to paper webs and the like to provide an easy-release surface. The method can be employed to measure coat weight and/or uniformity of spread of the coating.

2. Description of the Prior Art

Coatings are often applied to paper and similar substrates to produce coated webs for many different uses. For example, a coating composition of pigment (such as clay) and adhesive (such as starch) can produce a coated paper ideally suited for printing. Coated papers are also used in special applications, such as for release paper where the coating prevents another material from adhering too tightly to the coated paper. A common coating for release purposes is a cured polysiloxane resin, commonly referred to as a "silicone" coating.

In commercial coating processes, the coatings are applied to paper at high speeds where operating variables sometime result in a varying amount of coat weight and in poor coating uniformity. Typical quality control standards require the coating to be reasonably uniform in spread and within a desired coat weight range. Determination of such coating quality is usually not possible by visual observation, because the applied coating does not stand out sufficiently on the paper substrate upon which it is coated.

Prior art methods of coat weight include the use of a beta gauge technique or the coating consumption technique. The beta gauge technique is described in U.S. Pat. Nos. 3,019,336 and 3,130,303. The coating consumption technique is reasonably accurate, but the results obtained only yield an average cost weight over a given period of time with no indication of coat weight variation on the web in either the cross direction or machine direction of the web. Neither the beta gauge technique nor the coating composition technique is capable of determining spread uniformity of the coating.

One technique for detecting the location and spread uniformity of a coating is disclosed in U.S. Pat. No. 3,675,015 to Geib. The Geib patent discloses a method of evaluating the location and uniformity of a normally transparent abherent coating on a substrate by incorporating a fluorescent dye into the coating formulation and then viewing the coated object under ultraviolet light. One advantage of using fluorescent dyes is that the dye is not readily observed with the naked eye, but is observable when illuminated with ultraviolet (UV) light. Therefore, the coating operator can detect the coating with an inexpensive UV apparatus, but purchasers or users of the coated material will not notice the dye.

In a manner similar to that of Geib, U.S. Pat. No. 3,118,060 to Klein and U.S. Pat. No. 3,956,630 to Mellows disclose methods for determining coat weight by application of a fluorescent dye into the coating material and measuring the level of fluorescence in the coating. The level of fluorescence has been found to be reasonably proportional to the coat weight.

The use of fluorescent dyes to determine coating uniformity and coat weight is quite useful, because it is a non-destructive technique that can give immediate readings of the coating quality and because it does not detract from the appearance of the product. Furthermore, it can be used to identify coated paper products after they have been sold. Unfortunately, fluorescent dyes have not been found satisfactory for detecting coatings of cured polysiloxane resins, commonly used for release papers, for one or more of the following reasons. 1. The dyes inhibit curing of the silicone coatings. 2. The dyes do not always fluoresce in silicone coatings. 3. If the dyes do fluoresce in silicone coatings, they often have unacceptably low fluorescence levels. 4. The dyes frequently loose their fluorescence when the silicone coatings are cured. 5. The dyes do not disperse adequately in the silicone coatings.

SUMMARY OF THE INVENTION

It is an object of the invention to provide a rapid, nondestructive testing technique for detecting silicone coatings. It is a further object of the invention to provide such a testing technique which uses a fluorescent material added to the coatings. These and other objects are accomplished by the present invention, which is a method of detecting a cured silicone coating applied to a paper substrate or the like in web form, comprising:

adding an effective amount of a fluorescent pigment to the silicone coating formulation to be applied to the substrate;

applying the coating to the substrate;

curing the silicone coating;

scanning the coated surface of the substrate with a UV light source; and detecting the fluorescence of the coating.

The invention surprisingly provides a satisfactory detection method using fluorescent materials in a silicone coating without the above-stated disadvantages. This is believed to be true because the fluorescent pigments, in contrast to conventionally used fluorescent dyes, are physically tied into the silicone coatings. It is also believed that the dyes are not sufficiently heat stable at the silicone cure temperatures. Using a UV light source, the fluorescence can be detected with the naked eye (particularly suitable for observing spread uniformity and detecting skip spots) or it can be measured with a light meter.

The invention is also a method of measuring the coat weight of a silicone coating applied to a paper substrate or the like in web form comprising:

(a) adding an effective amount of a fluorescent pigment to the coating formulation to be applied to the substrate;

(b) applying the fluorescent pigment containing coating formulation to samples of the paper substrate at different coat weights over the coat weight range desired;

(c) curing the coating on the paper substrate;

(d) scanning the coated surface of the coated samples with a UV light source;

(e) measuring the fluorescence of the coated samples;

(f) comparing the fluoresence readings obtained with the actual coat weight applied to the samples as measured from an independent method;

(g) preparing a plot of coat weight versus fluorescence for the coatings applied; and (h) thereafter coating the substrate with the coating formulation and measuring the fluorescence of the coating applied for determining the coat weight applied.

The invention is also a coated paper product, comprising a paper substrate having thereon a cured coating composition comprising silicone and from 1% to 15%, based on the dry weight of the coating of fluorescent pigment. The coated product is ideally suited for being able to detect the coating at a later date, for example if a customer complains about the performance of the product. Spread uniformity, coat weight, and even coating or manufacturer identification can be detected. At the same time, the fluorescent pigment will not be observed by the customer, since it does not fluoresce sufficiently in ordinary light.

In accordance with the general principles of the present invention when it is used to measure coat weight, a fluorescent pigment is added to a silicone coating formulation and the level of fluorescence of the applied coating is continuously and quantatively measured by exposing it to UV light and measuring the fluorescing light with a light meter. The amount of coating applied is also determined by an independent off-machine process such as chemical analysis or ash determination, and the fluorescent readings are related to the coat weight as measured by the independent method to obtain a plot of fluorescence versus coat weight over the coat weight range desired. The object, of course, is to obtain a linear plot for the particular coating formulation over the coat weight range desired for maximum accuracy. After this step is performed, a fluorescent light reading device can then be calibrated directly with coat weight numbers or the plot can be kept at hand for ready reference.

A reference plot is required for each coating formulation, and in each case, the type of fluorescent pigment selected, the amount of fluorescent pigment added to the coating and the sensitivity of the UV light system used all play a role in obtaining the most accurate plot over the desired coat weight range. However, after the fluorescent data for a given coating formulation is obtained, fluorescence readings taken in the cross direction and the machine direction of the web give an accurate indication of the coating lay on the web. The amount of fluorescent pigment to be added to the silicone coating formulation is from 1% to 15%, and preferably between 3% and 7%.

DESCRIPTION OF THE PREFERRED EMBODIMENTS

Figure 1:
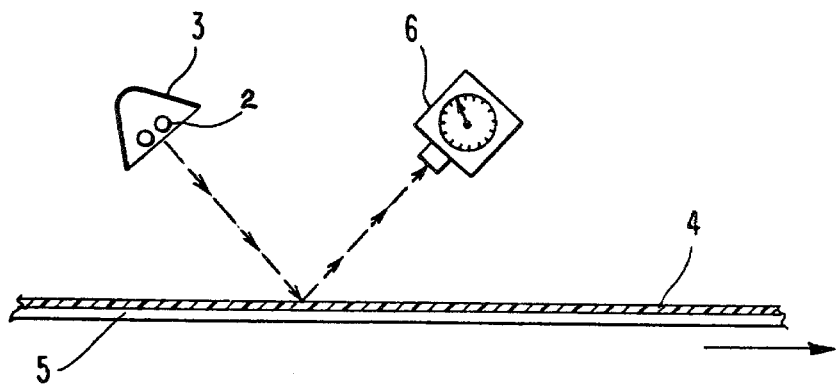
FIG. 1 is a schematic illustration of an apparatus which can be employed to practice the method of the invention to measure coat weight applied to a paper web.

The mechanism of the present invention relies on the principle of fluorescence which may be defined as the production of visible light by a substance as the result of exposure to and absorption of other radiation of a shorter wave length (such as ultraviolet light). The preferred fluorescing material for the invention is a fluorescent compound which absorbs ultraviolet light and emits it as a visible light. The fluorescent dyes used in the prior art are typically organic soluble materials containing an anthracene ring system in which the 9 and 10 carbons are replaced by such groups as CH,O,N,NH, and S that tend to contribute to the $\pi$-electron systems.

Fluorescent pigments are based on dilute solutions of fluorescent dyes, such as xanthene (rhodamine) or the aminonaphthalimides, prepared in triazine-modified sulfonamide resins. This resin type is an extremely friable organic glass that is formed by cocondensing a toluene sulfonamide-formaldehyde with a triazine such as melamine or benzoguanamine. Other fluorescent pigments are based on solutions of fluorescent dyes and modified glyceryl phthalate or vinyl resins. There are also a limited number of organic compounds that exhibit fluorescence in their undissolved state. Among these are the aldazines of certain aromatic aldehydes such as 2-hydroxy-1-naphthaldehyde. Thus, as used in the specification and claims, the term "fluorescent pigment" means a particle which remains in its particulate form and does not dissolve in the coating composition and which exhibits fluorescence due to having attached thereto fluorescent dyes or due to its own fluorescence.

The size of fluorescent pigments typically averages from about 1.2 micrometers to about 4 micrometers. They can be produced by either coloring the resin in the fused state, or dyeing a powdered resin or resin precipitate in a dye bath. Examples of their production are disclosed in U.S. Pat. No. 2,809,954; Canadian Patent No. 562,729; British Pat. No. 770,889; U.S. Pat. No. 2,851,423; British Pat. No. 712,219; and U.S. Pat. No. 3,518,205.

In order to demonstrate the present invention, the following examples are provided.

EXAMPLE I

A silicone coating formulation was prepared with a fluorescent pigment added at a known concentration and coated at 6.8% solids on 5.0 mil aluminum foil in various coating weights using different Meyer bar numbers. The coating was prepared from the following formulation:

| | |
|---|---|
| Naphtha | 149.31 grams |
| Hexane | 49.77 grams |
| Dow Corning's Syloff 23-30 (dimethylpolysiloxane silicone rubber polymer, 30% in Xylene) | 22.88 grams |
| Dow Corning's Syloff 292 (silicone rubber polymer) | 22.88 grams |
| Dow Corning's Syloff 297 (anchorage additive, organo-functional silane) | 1.09 grams |
| Dow Corning's C-4-2117 (fast cure additive, reactive cross-linking silane) | 1.64 grams |
| Dow Corning's XY-176 (organo-tin ester catalyst for silicone rubber) | 1.64 grams |
| Hercules' Radiant Fluorescent Orange Pigment P-1600 513 | 1.10 grams (6.64% of the total dry silicone solids) |

Curing of the silicone coating was done at 300° F. for 30 seconds. The ultraviolet fluorescence or fluorescent brightness of each sample was measured by the apparatus illustrated in FIG. 1, which consists of two General Electric fluorescent strips 2, W/BLBF4P5, black light blue fluorescent 4", 5 watts, projected by reflector 3 onto the coating 4 of paper web 5 and a light meter 6, provided by a Triplet meter Model No. 420R, 0–50 microamps built-in resistance of 825 ohms, measuring the visible wave light fluorescing from the coating 4. The brightness readings were unitless, but proportional to the amount of fluorescence.

The silicone coating was then removed from the aluminum foil and the actual amount of silicone applied (lbs./3,300 ft$^2$) for each Meyer bar application was gravimetrically determined. Subtracting the UV fluorescent brightness of the uncoated aluminum foil from that of the aluminum foil plus silicone coating provided a direct correlation of UV flourescent brightness vs. silicone coat weight (lbs. /3,300 ft$^2$). A graph for UV fluorescent brightness vs. silicone coat weight was plotted and found to provide a reliable means of determining coat weight on other coating applications using the same concentration of fluorescing pigment.

This procedure was then repeated on a paper web body stock. After subtracting the body stock UV fluorescent brightness reading from the body stock plus silicone coating UV fluorescent brightness reading, the coating weight was determined from the previously prepared graph.

The coatings tested resulted in the following:

| | Aluminum Foil | |
|---|---|---|
| Meyer Bar No. | UV Fluorescent Brightness (B/S 8.3) | Silicone Coat Weight (pounds/3,300 ft$^2$) Gravimetric Reading |
| 0 | 8.3 | 0.00 |
| 5 | 9.2 | 0.25 |
| 10 | 9.9 | 0.51 |
| 16 | 10.5 | 0.73 |
| 20 | 11.0 | 1.06 |
| 30 | 12.0 | 1.48 |

| | Paper Web | |
|---|---|---|
| Meyer Bar No. | UV Fluorescent Brightness (B/S 7.3) | Silicone Coat Weight (pounds/3,300 ft$^2$) Graph Reading |
| 0 | 7.5 | .06 |
| 5 | 9.2 | .61 |
| 10 | 10.3 | 1.01 |
| 16 | 12.0 | 1.75 |
| 20 | 13.2 | 2.36 |
| 30 | 14.4 | 2.98 |

Figure 2:
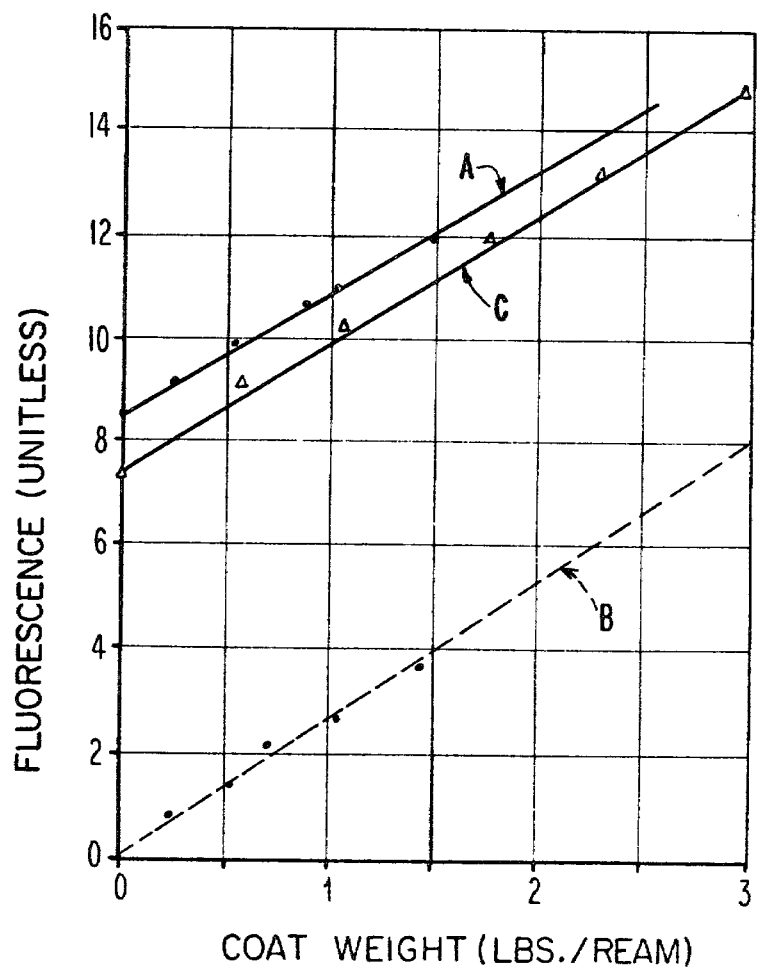
FIG. 2 is a plot of fluorescence vs. coat weight for the silicone coated web described in Example I below.

The UV fluorescence readings for Example I were plotted in a graph illustrated in FIG. 2, where Curve A represents the actual brightness readings for the coating on aluminum foil plotted against the coat weight as determined by gravimetric measurements. Curve B represents the readings of Curve A corrected to subtract the UV brightness reading of the bare aluminum foil. Curve C represents the actual brightness readings for the coating on a paper web plotted against the coat weight as determined from Curve B after subtracting the UV brightness reading of the base paper before coating.

EXAMPLE II

The procedures of Example I were repeated except that Dow Corning C-4-2115 and Syloff 23 in a 50-50 mixture provided the dimethylpolysiloxane based release coating and the fluorescent pigment was provided by Radiant Fluorescent Chartreuse Pigment P-1600-510, manufactured by Radiant Color Division, Hercules, Inc. The fluorescent pigment of Example II was applied in a 6.64% concentration (as in Example I) and also in a 3.32% concentration. In both cases, the fluorescent pigment was found suitable for visual observation of coating uniformity and coat weight measurements by the apparatus of FIG. 1.

EXAMPLE III

A 100% solventless silicone release coating comprised of copolymers of dimethyl and vinylmethylpolysiloxanes (Dow Corning Q27044/Q27069) and containing 6.64% Radiant Fluorescent Pigment Orange P-1600-513 (Radiant Color Division of Hercules, Inc.) was coated at various coat weights and cured onto paper bodystock using a blade coater. The procedure was repeated using an offset gravure roll to apply first the same coating mixture and then the same coating modified to have only 3.32% fluorescent pigment concentration. In all three cases, both coat weight and coating uniformity were found to be detachable by the present invention.

EXAMPLE IV

The procedures of Example III were repeated, except that a 100% solventless silicone release coating using General Electric SS4300/SS4305 silicone blend was used in place of the Dow Corning silicone system. The coatings having both 6.64% and 3.32% fluorescent pigment concentration were coated by gravure roll, and coating uniformity and coat weight were found to be detachable in both cases by the present invention.

Other fluorescent pigments were used with the silicone coatings of Examples III and IV and found satisfactory for detecting coat weight and uniformity by the present invention. The fluorescent pigments tested were: Hi-Viz B-3530, B-3030, and 2830, all three of which are cerise red and manufactured by Lawter Chemicals, Inc., of Chicago, Illinois; and Hercules P-1700-610 chartreuse and P-1600-511 green, both of which are manufactured by Radiant Color Division of Hercules, Inc.

For comparative purposes, fluorescent dyes (instead of fluorescent pigments) were added to the silicone release coatings of both the solvent-type (polydimethylsiloxane) and the solventless-type (copolymer of dimethyl and vinyl methyl polysiloxanes). The fluorescent dyes were found to exhibit the following unacceptable properties which prevent or make undesirable their use for silicone coat weight and uniformity determinations.

| I | II | III | IV | V |
|---|---|---|---|---|
| They inhibited silicone coating cure | They did not fluoresce in the silicone coating | They had unacceptably low fluorescence | They lost fluorescence when the silicone coating was cured | They did not disperse sufficiently in the silicone coating |

The following materials were applied to paper bodystock in the manner described in Example IV, but in the concentration indicated.

| Dyestuff | Conc. | Color Index Description | Manufacturer | Trait (See Above) |
|---|---|---|---|---|
| Calcofluor White RW | 0.1% | Fluorescent Brightener 61 | American Cyanamid | I, IV, V |
|  | 1.0% |  |  | I, IV, V |
|  | 1.5% |  |  | I, IV, V |
| Calcofluor White CBP | 1.5% | Fluorescent Brightener | American Cyanamid | I, V |
| Calcofluor White 9262L | 1.5% | Fluorescent Brightener | American Cyanamid | I, V |
| Fluorescein | 1.5% | Acid Yellow 73 (CI #45350) |  | II |
| Rhodamine 6GDN | 1.5% | Basic Red 1 (CI #45160) | EI Dupont Co. | V |
| Rhodamine B-Extra | 1.5% | Basic Violet 10 (CI #45170) | EI Dupont Co. | V |
| Sulpho- (Solvent) Rhodamine B | 1.5% | Not Listed | American Hoechst Corp. | V |
| Anthracene | 1.5% | Mordant Dye |  | IV, V |
| Imidazole | 1.5% |  |  | IV, V |
| Anthraquinone | 1.5% |  |  | IV, V |
| Leucophor SF Granules | 1.5% | Fluorescent Brightener | Sandoz | IV, V |

I claim:

1. A method of detecting a cured silicone coating applied to a paper substrate or the like in web form comprising:
   adding an effective amount of a fluorescent pigment to the silicone coating formulation to be applied to the substrate;
   applying the coating to the substrate;
   curing the silicone coating;
   scanning the coated surface of said substrate with a UV light source; and
   detecting the fluorescence of the coating.

2. A method of measuring the coat weight of a silicone coating applied to a paper substrate or the like in web form comprising:
   (a) adding an effective amount of a fluorescent pigment to the silicone coating formulation to be applied to a substrate;
   (b) applying the fluorescent pigment containing silicone coating formulation to samples of the paper substrate at different coat weights over the coat weight range desired;
   (c) curing the coating on the paper substrate;
   (d) scanning the coated surface of the coated samples with a UV light source;
   (e) measuring the fluorescence of the coated samples;
   (f) comparing the fluorescence readings obtained with the actual coat weights applied to the samples as measured from an independent method;
   (g) preparing a plot of coat weight versus fluorescence for the coatings applied; and
   (h) thereafter coating the paper substrate with the silicone coating formulation and measuring the fluorescence of the coating applied for determining the coat weight applied.

* * * * *